(12) United States Patent
Kurokawa et al.

(10) Patent No.: US 10,494,318 B2
(45) Date of Patent: Dec. 3, 2019

(54) METHOD FOR MANUFACTURING CONJUGATED DIENE, AND REACTION DEVICE

(71) Applicants: JXTG NIPPON OIL & ENERGY CORPORATION, Tokyo (JP); NATIONAL UNIVERSITY CORPORATION SAITAMA UNIVERSITY, Saitama (JP)

(72) Inventors: Hideki Kurokawa, Saitama (JP); Tatsuya Ichijo, Tokyo (JP); Nobuhiro Kimura, Tokyo (JP)

(73) Assignees: JXTG NIPPON OIL & ENERGY CORPORATION, Tokyo (JP); NATIONAL UNIVERSITY CORPORATION SAITAMA UNIVERSITY, Saitama (JP)

( * ) Notice: Subject to any disclaimer, the term of this patent is extended or adjusted under 35 U.S.C. 154(b) by 171 days.

(21) Appl. No.: 15/559,639

(22) PCT Filed: Mar. 18, 2016

(86) PCT No.: PCT/JP2016/058835
§ 371 (c)(1),
(2) Date: Sep. 19, 2017

(87) PCT Pub. No.: WO2016/152810
PCT Pub. Date: Sep. 29, 2016

(65) Prior Publication Data
US 2018/0339953 A1  Nov. 29, 2018

(30) Foreign Application Priority Data
Mar. 26, 2015  (JP) .................. 2015-064164

(51) Int. Cl.
| | | |
|---|---|---|
| *C07C 5/333* | (2006.01) | |
| *B01J 37/02* | (2006.01) | |
| *B01J 37/03* | (2006.01) | |
| *B01J 37/18* | (2006.01) | |
| *B01J 35/00* | (2006.01) | |
| *B01J 23/00* | (2006.01) | |
| *B01J 23/62* | (2006.01) | |
| *B01J 35/02* | (2006.01) | |
| *B01J 37/00* | (2006.01) | |

(52) U.S. Cl.
CPC ........... *C07C 5/3335* (2013.01); *B01J 23/002* (2013.01); *B01J 23/626* (2013.01); *B01J 35/0006* (2013.01); *B01J 35/023* (2013.01); *B01J 35/026* (2013.01); *B01J 37/0063* (2013.01); *B01J 37/0205* (2013.01); *B01J 37/0236* (2013.01); *B01J 37/03* (2013.01); *B01J 37/18* (2013.01); *C07C 5/3337* (2013.01); *B01J 2523/00* (2013.01); *C07C 2521/04* (2013.01); *C07C 2523/14* (2013.01); *C07C 2523/42* (2013.01); *C07C 2523/62* (2013.01)

(58) Field of Classification Search
CPC . C07C 5/3335; C07C 5/3337; C07C 2523/14; C07C 2523/42; C07C 2523/62; C07C 2521/04; B01J 37/0063; B01J 37/0205; B01J 37/0236; B01J 37/03; B01J 37/18; B01J 23/002; B01J 23/626; B01J 35/0006; B01J 35/023; B01J 35/026; B01J 2523/00
See application file for complete search history.

(56) References Cited

U.S. PATENT DOCUMENTS

| | | | |
|---|---|---|---|
| 2,433,800 A | 12/1947 | Watson | |
| 3,801,671 A | 4/1974 | Marsheck | |
| 2004/0015031 A1* | 1/2004 | Messenger | .............. C07C 5/48 585/658 |
| 2014/0309470 A1* | 10/2014 | Park | ..................... B01J 23/626 585/660 |

FOREIGN PATENT DOCUMENTS

| | | |
|---|---|---|
| JP | S27-001758 A | 12/1947 |
| JP | S57-140730 A | 8/1982 |
| JP | S60-001139 A | 1/1985 |
| JP | 2003-220335 A | 8/2003 |
| JP | 2014-205135 A | 10/2014 |

OTHER PUBLICATIONS

Translation of Kikuchi et al. "Effect of Sn Addition on n-Butane Dehydrogenation over Alumina-supported Pt Catalysts Prepared by Co-impregnation and Sol-gel Methods" Journal of the Japan Petroleum Institute, 2012, vol. 55, No. 3 p. 206-213 (Year: 2012).*
International Search Report from Application No. PCT/JP2016/058835 dated Jun. 6, 2016 and Written Opinion dated Oct. 5, 2017.
Kikuchi et al., Journal of the Japan Petroleum Institute, 2012, p. 206-p. 213, vol. 55.

* cited by examiner

*Primary Examiner* — In Suk C Bullock
*Assistant Examiner* — Jason Y Chong
(74) *Attorney, Agent, or Firm* — Greenblum & Bernstein, P.L.C.

(57) ABSTRACT

A method for producing a conjugated diene according to one aspect of the present invention comprises a step of contacting a raw material gas containing an alkane with a first catalyst and a second catalyst in this order to obtain a product gas containing a conjugated diene. In the production method, the first catalyst contains Sn and Pt, and a content of Sn in the first catalyst is less than 12% by mass based on the total mass of the first catalyst; and the second catalyst contains Sn and Pt, and a content of Sn in the second catalyst is 12% by mass or more based on the total mass of the second catalyst.

5 Claims, No Drawings

METHOD FOR MANUFACTURING CONJUGATED DIENE, AND REACTION DEVICE

TECHNICAL FIELD

The present invention relates to a method for producing a conjugated diene and a reaction device.

BACKGROUND ART

An increase in the demand of a conjugated diene including butadiene as a raw material for synthetic rubbers, or the like has been anticipated because of motorization centering on Asia in recent years. For example, a method for subjecting n-butane to a direct dehydrogenation reaction using a dehydrogenation catalyst to produce a conjugated diene (Patent Literature 1) and a method for subjecting n-butene to an oxidative dehydrogenation reaction to produce a conjugated diene (Patent Literatures 2 to 4) have been known as a method for producing a conjugated diene.

CITATION LIST

Patent Literature

Patent Literature 1: Japanese Unexamined Patent Publication No. 2014-205135
Patent Literature 2: Japanese Unexamined Patent Publication No. S57-140730
Patent Literature 3: Japanese Unexamined Patent Publication No. S60-1139
Patent Literature 4: Japanese Unexamined Patent Publication No. 2003-220335

SUMMARY OF INVENTION

Technical Problem

Along with the increase in the demand of conjugated dienes, the development of various methods for producing conjugated dienes is required, the method having different features such as demand characteristics, operating cost, and reaction efficiency of a producing device.

An object of the present invention is to provide a method for producing a conjugated diene which can efficiently produce a conjugated diene from an alkane as a novel production method of a conjugated diene. Another object of the present invention is to provide a reaction device capable of suitably conducting the production method.

Solution to Problem

The present inventors have found that excellent dehydrogenation activity is obtained by combining a specific catalyst in which the content of Sn is less than 12% by mass with a specific catalyst in which the content of Sn is 12% by mass or more in a step of obtaining a conjugated diene from an alkane, and the present invention has thus been completed.

That is, a method for producing a conjugated diene according to one aspect of the present invention comprises a step of contacting a raw material gas containing an alkane with a first catalyst and a second catalyst in this order to obtain a product gas containing a conjugated diene. In the production method, the first catalyst contains Sn and Pt, and a content of Sn in the first catalyst is less than 12% by mass based on the total mass of the first catalyst; and the second catalyst contains Sn and Pt, and a content of Sn in the second catalyst is 12% by mass or more based on the total mass of the second catalyst.

According to the production method, the conjugated diene can be efficiently obtained from the alkane. The present inventors speculate a cause by which such an effect is obtained, as follows. First, a raw material gas containing an alkane is brought into contact with a first catalyst, so that the dehydrogenation reaction of the alkane proceeds at a high conversion rate, thereby producing an olefin at a high selection rate. Next, a gas containing the produced olefin is brought into contact with the second catalyst, so that the dehydrogenation reaction of the olefin proceeds at a high conversion rate, thereby producing the conjugated diene at a high selection rate. The present inventors speculate that the conjugated diene can be obtained at a high yield according to the production method of the present invention in the above a mechanism.

In one aspect, the first catalyst may have a first support containing Al; and the second catalyst may have a second support containing Al. By using the first catalyst and the second catalyst, the effect of the present invention is more remarkably exhibited.

In one aspect, a metal content of Pt in the first catalyst may be 0.05% by mass or more and 3% by mass or less based on the total mass of the first catalyst; and a metal content of Pt in the second catalyst may be 0.05% by mass or more and 3% by mass or less based on the total mass of the second catalyst. By using the first catalyst and the second catalyst, the effect of the present invention is more remarkably exhibited.

In one aspect, the alkane may be an alkane having 4 to 10 carbon atoms.

In one aspect, the alkane and the conjugated diene may be butane and butadiene, respectively. The production method can be particularly suitably employed as a method for producing butadiene.

A reaction device according to another aspect of the present invention is a reaction device for obtaining a product gas containing a conjugated diene from a raw material gas containing an alkane. The reaction device comprises: a first catalyst layer containing a first catalyst; and a second catalyst layer containing a second catalyst. In the reaction device, the first catalyst contains Sn and Pt, and a content of Sn in the first catalyst is less than 12% by mass based on the total mass of the first catalyst; and the second catalyst contains Sn and Pt, and a content of Sn in the second catalyst is 12% by mass or more based on the total mass of the second catalyst.

A reaction device according to still another aspect of the present invention is a reaction device for obtaining a product gas containing a conjugated diene from a raw material gas containing an alkane. The reaction device comprises a catalyst layer containing a first catalyst and a second catalyst. In the reaction device, the first catalyst contains Sn and Pt, and a content of Sn in the first catalyst is less than 12% by mass based on the total mass of the first catalyst; and the second catalyst contains Sn and Pt, and a content of Sn in the second catalyst is 12% by mass or more based on the total mass of the second catalyst.

Advantageous Effects of Invention

The present invention can provide a method for producing a conjugated diene which can efficiently produce conjugated diene from an alkane as a novel producing method of a conjugated diene.

DESCRIPTION OF EMBODIMENTS

Hereinafter, one suitable embodiment of the present invention will be described. However, the present invention is not limited to the following embodiment at all.

A production method according to the present embodiment is a production method comprising a step of contacting a raw material gas containing an alkane with a first catalyst and a second catalyst in this order to obtain a product gas containing a conjugated diene. In the production method, the first catalyst contains tin (Sn) and platinum (Pt), and a content of Sn in the first catalyst is less than 12% by mass based on the total mass of the first catalyst; and the second catalyst contains Sn and Pt, and a content of Sn in the second catalyst is 12% by mass or more based on the total mass of the second catalyst.

According to the production method according to the present embodiment, the conjugated diene can be efficiently obtained from the alkane. That is, in the production method according to the present embodiment, the alkane is reacted at a high conversion rate while catalyst deterioration is suppressed, so that the conjugated diene can be obtained at a high selection rate. For this reason, in the production method according to the present embodiment, the conjugated diene can be obtained at a high yield while the replacement or reproduction frequency of the catalyst is reduced.

Herein, the conversion rate of the alkane, the selection rate of the conjugated diene, and the yield of the conjugated diene are defined by the following formulae (1), (2), and (3).

$$r_C = \{1-(m_1/m_0)\} \times 100 \quad (1)$$

$$r_S = \{m_2/(m_0-m_1)\} \times 100 \quad (2)$$

$$r_Y = (m_2/m_0) \times 100 \quad (3)$$

$r_C$ in the formula (1) is the conversion rate of the alkane. $m_0$ is the number of moles of the alkane contained in the raw material gas. $m_1$ is the number of moles of the alkane remaining in the product gas.

$r_S$ in the formula (2) is the selection rate (%) of the conjugated diene. $m_2$ is the number of moles of the conjugated diene contained in a product material (product gas).

$r_Y$ in the formula (3) is the yield (%) of the conjugated diene.

In the production method according to the present embodiment, the raw material gas contains the alkane. The number of carbons of the alkane may be the same as that of the intended conjugated diene. That is, the alkane may be a hydrocarbon compound obtained when all double bonds which are present in the conjugated diene assumed as a product material are hydrogenated. The number of carbons of the alkane may be 4 to 10, or 4 to 6, for example.

The alkane may be, for example, chain-like or cyclic. The chain-like alkane may be at least one selected from the group consisting of butane, pentane, hexane, heptane, octane, and decane, for example. The cyclic alkane may be at least one selected from the group consisting of cyclopentane, cyclohexane, cycloheptane, cyclooctane, cyclodecane, and methylcyclohexane, for example. More specifically, the chain-like alkane may be linear or branched. The linear alkane may be at least one selected from the group consisting of n-butane, n-pentane, n-hexane, n-heptane, n-octane, and n-decane. The branched alkane may be at least one selected from the group consisting of isobutane, isopentane, 2-methylpentane, 3-methylpentane, 2,3-dimethylpentane, isoheptane, isooctane, and isodecane. The raw material gas may contain the alkanes singly or in combinations of two or more.

In the raw material gas, the partial pressure of the alkane may be 1.0 MPa or less, or 0.01 MPa or less. By decreasing the partial pressure of the alkane of the raw material gas, the conversion rate of the alkane is likely to be further improved.

The partial pressure of the alkane in the raw material gas is preferably 0.001 MPa or more, and more preferably 0.005 MPa or more from the viewpoint of reducing the size of a reactor with respect to a raw material flow rate.

The raw material gas may further contain an inactive gas such as nitrogen or argon, and may further contain steam.

When the raw material gas contains the steam, the content of the steam is preferably 1.0 times moles or more, and more preferably 1.5 times moles or more with respect to the alkane. By incorporating the steam in the raw material gas, deterioration in the activity of the catalyst may be more remarkably suppressed. The content of the steam may be, for example, 50 times moles or less, and is preferably 10 times moles or less with respect to the alkane.

The raw material gas may further contain other ingredients such as hydrogen, oxygen, carbon monoxide, carbon dioxide, alkanes, and dienes in addition to the above.

In the production method according to the present embodiment, the product gas contains the conjugated diene. Examples of the conjugated diene obtained by the production method according to the present embodiment include 1,3-butadiene, 1,3-pentadiene, isoprene, 1,3-hexadiene, 1,3-heptadiene, 1,3-octadiene, 1,3-nonadiene, and 1,3-decadiene.

The production method according to the present embodiment can be particularly suitably used for a method using a raw material gas containing butane as an alkane among the above, that is, a method for producing 1,3-butadiene. The butane used for producing 1,3-butadiene may be n-butane or a mixture of n-butane and isobutane.

The production method according to the present embodiment comprises a step of contacting the raw material gas with the first catalyst and the second catalyst in this order to obtain the product gas containing a conjugated diene. Hereinafter, the first catalyst and the second catalyst will be described in detail.

The first catalyst is a catalyst containing Sn and Pt, and the content $C_{S1}$ of Sn in the first catalyst is less than 12% by mass based on the total mass of the first catalyst. It is considered that, according to the first catalyst, the dehydrogenation reaction to the olefin from the alkane efficiently proceeds, and the conjugated diene can be efficiently produced from the alkane by using such a first catalyst and the second catalyst to be described later in combination.

The reason why the above-mentioned effect is exhibited when the content $C_{S1}$ of the first catalyst is less than 12% by mass is not necessarily clear, but this is considered to be because the exposure of a Pt active point is relatively increased when the content $C_{S1}$ is decreased, so that the reactivity of the alkane is improved.

The content $C_{S1}$ of Sn in the first catalyst may be 11% by mass or less based on the total mass of the first catalyst. According to the first catalyst, the alkane can be converted to the olefin at higher efficiency.

The content $C_{S1}$ of Sn in the first catalyst may be 1.0% by mass or more, or 3.0% by mass or more, based on the total mass of the first catalyst. In the first catalyst according to the present embodiment, it is considered that Sn and Pt form bimetallic particles to dilute Pt atoms in the particles, so that the cleavage reaction of a C—C bond caused by the Pt atoms acting on one molecule of the alkane at multiple points is suppressed. Thereby, it is considered that the activity with respect to the intended reaction is improved.

The content $C_{P1}$ of Pt in the first catalyst may be 3.0% by mass or less, or 2.0% by mass or less based on the total mass of the first catalyst. In such a dehydrogenation catalyst, Pt particles formed on the catalyst have a size suitable for the dehydrogenation reaction, to increase the surface area of platinum per unit platinum weight, so that a more efficient reaction system can be achieved.

The content $C_{P1}$ of Pt in the first catalyst may be 0.05% by mass or more, or 0.2% by mass or more, based on the total mass of the first catalyst. According to the first catalyst, the amount of platinum per catalyst amount is increased, so that the size of a reactor can be reduced.

In the first catalyst, the ratio ($C_{S1}/C_{P1}$) of the content $C_{S1}$ to the content $C_{P1}$ is preferably 3.0 or more, and more preferably 5.0 or more. The ratio ($C_{S1}/C_{P1}$) may be 12 or less, or 10 or less. When the ratio ($C_{S1}/C_{P1}$) is within the range, the reaction to the olefin from the alkane tends to be likely to further proceed.

The first catalyst may contain other metal elements in addition to Sn and Pt. Examples of the other metal elements include Li, Na, K, Mg, Ca, Zn, Fe, Pb, In, Se, Sb, Ni, Ga, Ge, and Al. Each of the metal elements in the first catalyst may be present as a single oxide, may be present as a composite oxide with other metal, or may be present as a metal simple substance.

When the first catalyst contains Al, the content $C_{A1}$ of Al in terms of oxide in the first catalyst may be 20% by mass or more, or 50% by mass or more based on the total mass of the first catalyst. The content $C_{A1}$ may be 99% by mass or less, or 95% by mass or less.

When the first catalyst contains Mg, the content $C_{M1}$ of Mg in terms of oxide in the first catalyst may be 1.0% by mass or more, or 5.0% by mass or more based on the total mass of the first catalyst. The content $C_{M1}$ may be 80% by mass or less, or 50% by mass or less.

The content of each of the metal elements in the first catalyst can be confirmed by analyzing the first catalyst according to a method described in the following Examples.

The first catalyst may be a catalyst having a first support and a supported metal supported on the support, for example. At this time, the first catalyst has Pt as the supported metal. In the first catalyst, Sn may be contained in the first support or may be contained as the supported metal.

The first support may be a metal oxide support containing Al, for example. The metal oxide support may contain Li, Na, K, Mg, Ca, Zn, Fe, Pb, In, Se, Sb, Ni, Ga, Ge, Pt, and Sn or the like, for example, in addition to Al.

The metal oxide support may be a support containing alumina ($Al_2O_3$), or a support containing a composite oxide of Al and another metal, for example. More specifically, the metal oxide support may be a support containing a metal oxide such as alumina, a composite oxide of Al and Mg, a composite oxide of Al and Sn, a composite oxide of Al and Pb, or a composite oxide of Al and Zn, Se, Fe or In or the like, for example. The metal oxide support may contain the metal oxides singly or in combinations of two or more.

Examples of a method for preparing the support include, but not particularly limited to, a sol gel method, a coprecipitation method, and a hydrothermal synthesis method.

One aspect of the method for preparing the support will be shown below. First, a solution in which a metal precursor of an intended metal element is dissolved in a solvent is prepared. Next, ion exchange water is dropped into the solution while the solution is stirred. Then, the solution is stirred while the solution is heated under reflux, to hydrolyze the metal precursor, and the solvent is then removed under reduced pressure to obtain a solid. By drying the obtained solid, and thereafter firing the dried solid, the support containing the intended metal element is obtained. When a support containing a plurality of metal elements is prepared, a mixed solution may be used, which is obtained by preparing a solution in which a metal precursor is dissolved in a solvent for each of the plurality of metal elements, and mixing the solutions. By dissolving metal precursors of a plurality of metal elements in the same solvent, a mixed solution may be prepared.

The precursor of the metal may be a salt or complex containing the metal element, for example. The salt containing the metal element may be at least one selected from the group consisting of an inorganic salt, an organic acid salt, and hydrates thereof, for example. The inorganic salt may be at least one selected from the group consisting of a sulfate, a nitrate, a chloride, a phosphate, and a carbonate, for example. The organic salt may be at least one selected from the group consisting of an acetate and an oxalate, for example. The complex containing the metal element may be at least one selected from the group consisting of an alkoxide complex and an ammine complex, for example.

The solvent dissolving the metal precursor may be at least one selected from the group consisting of hydrochloric acid, nitric acid, ammonia water, and ethanol, for example.

Firing can be performed under air atmosphere or oxygen environment, for example. Firing may he performed at one stage, or multi stages of two stages or more. A tiring temperature may be a temperature at which a metal precursor can be decomposed. The firing temperature may be 200 to 1000° C., or 400 to 800° C., for example. When firing is performed at multi stages, at least one stage thereof may be performed at the firing temperature. A firing temperature at other stage may be within the same range as the above, for example, and may be 100 to 200° C.

In one aspect, the metal oxide support may be a support containing alumina. In this aspect, the content of Al in terms of oxide in the metal oxide support may be 20% by mass or more, or 50% by mass or more, based on the total mass of the metal oxide support.

In another aspect, the metal oxide support may be a support containing a composite oxide of Al and Mg. In this aspect, the content of Al in terms of oxide in the metal oxide support may be 20% by mass or more, 50% by mass or more, 99% by mass or less, or 95% by mass or less, based on the total mass of the metal oxide support. in this aspect, the content of Mg in terms of oxide in the metal oxide support may be 1.0% by mass or more, 5.0% by mass or more, 80% by mass or less, or 50% by mass or less, based on the total mass of the metal oxide support.

In still another aspect, the metal oxide support may be a support containing a composite oxide of Al and Sn. In this aspect, the content of Al in terms of oxide in the metal oxide support may be 20% by mass or more, 50% by mass or more, 99% by mass or less, or 95% by mass or less, based on the total mass of the metal oxide support. In this aspect, the content of Sn in terms of oxide in the metal oxide support may be 1.0% by mass or more, 3.0% by mass or more, 50% by mass or less, or 30% by mass or less, based on the total mass of the metal oxide support.

The acidity of the first support is preferably near neutrality from the viewpoint of suppressing a side reaction. Herein, the standard over the acidity of the support is generally distinguished by a pH in a state where the support is dispersed in water. That is, herein, the acidity of the support can be represented by the pH of a suspension in which 1% by mass of the support is suspended. The acidity of the first support may preferably have a pH of 5.5 to 8.5, and more preferably a pH of 6.0 to 8.0.

The specific surface area of the first support is preferably 30 m$^2$/g or more, and more preferably 50 m$^2$/g or more. The first support can advantageously increase the conversion rate of the alkane. The specific surface area of the first support may be 1000 m$^2$/g or less, or 500 m$^2$/g or less. The first support having such a specific surface area tends to have sufficient strength which can be suitably used industrially, and the conversion rate of the alkane tends to be further improved by using the support. The specific surface area of the first support is measured with a BET specific surface area meter using a nitrogen adsorption method, or the like.

The first catalyst may have one or two or more of supported metals supported on the first support. The supported metal supported on the first support may be supported as an oxide or a metal simple substance.

Examples of the supported metal supported on the first support include Pt, Sn, Zn, Se, Fe, in, Ga, Ge, and Pb. In the present embodiment, when the first support does not contain Sn, Pt and Sn are contained in the supported metal. When the first support contains Sn, the supported metal may contain Pt.

Examples of a method for supporting the metal on the first support include, but not particularly limited to, an impregnation method, a precipitation method, a coprecipitation method, a kneading method, an ionic exchange method, and a pore-filling method.

One aspect of the method for supporting the metal on the support will be shown below. First, a support is added into a solution in which a precursor of an intended supported metal is dissolved in a solvent (for example, alcohol), and the solution is then stirred. Then, the solvent is removed under reduced pressure to obtain a solid, and the solid is dried. By firing the dried solid, the intended metal can be supported on the support.

In the supporting method, the precursor of the supported metal may be a salt or complex containing the metal element, for example. The salt containing the metal element may be at least one selected from the group consisting of an inorganic salt, an organic acid salt, and hydrates thereof, for example. The inorganic salt may be at least one selected from the group consisting of a sulfate, a nitrate, a chloride, a phosphate, and a carbonate, for example. The organic salt may be at least one selected from the group consisting of an acetate and an oxalate, for example. The complex containing the metal element may be at least one selected from the group consisting of an alkoxide complex and an ammine complex, for example.

As conditions during stirring, for example, a stirring temperature can be set to 0 to 60° C., and a stirring time can be set to 10 minutes to 24 hours. As conditions during drying, for example, a drying temperature can be set to 100 to 250° C., and a drying time can be set to 3 hours to 24 hours.

Firing can be performed under air atmosphere or oxygen environment, for example. Firing may be performed at one stage, or multi stages of two stages or more. A firing temperature may be a temperature at which a precursor of a supported metal can be decomposed. The firing temperature may be 200 to 1000° C., or 400 to 800° C., for example. When firing is performed at multi stages, at least one stage thereof may be performed at the firing temperature. A firing temperature at other stage may be within the same range as the above, for example, and may be 100 to 200° C.

The amount of Pt supported on the first support (content of Pt in the first catalyst) is preferably 0.01 parts by mass or more, and more preferably 0.1 parts by mass or more with respect to 100 parts by mass of the first support. The amount of Pt supported on the first support may be 5.0 parts by mass or less, or 3.0 parts by mass or less with respect to 100 parts by mass of the first support. In such an amount of Pt, Pt particles formed on the catalyst have a size suitable for the dehydrogenation reaction, to increase the surface area of platinum per unit platinum weight, so that a more efficient reaction system can be achieved. In such an amount of Pt, high activity can be maintained over a longer period of time while catalyst cost is suppressed.

The degree of dispersion of Pt in the first catalyst may be 1.0% or more, and preferably 5.0% or more. By the first catalyst having such a degree of dispersion of Pt, a side reaction is further suppressed, so that high activity tends to be maintained over a longer period of time. The degree of dispersion of Pt in the first catalyst represents a value measured by a measuring method described in the following Examples.

In one suitable aspect, the first catalyst may be a catalyst having Sn and Pt supported on a first support containing Al (preferably, a metal oxide support containing alumina, or a composite oxide of Al and Mg), or a catalyst having Sn and Pt supported in this order.

In this aspect, the amount of Sn supported on the first support is preferably 1.0 part by mass or more, and more preferably 3.0 parts by mass or more with respect to 100 parts by mass of the first support. The amount of Sn supported on the first support may be 80 parts by mass or less, or 50 parts by mass or less with respect to 100 parts by mass of the first support. When the amount of Sn is within the range, catalyst deterioration is further suppressed, so that high activity tends to be maintained over a longer period of time.

The first catalyst may be molded by methods such as an extrusion molding method and a tablet compression method.

The first catalyst may contain a molding auxiliary agent in the range not to deteriorate the physical properties and catalytic performance of the catalyst from the viewpoint of improving moldability in a molding step. The molding auxiliary agent may be at least one selected from the group consisting of a thickener, a surfactant, a humectant, a plasticizer, and a binder raw material, for example. The molding step of molding the dehydrogenation catalyst may be performed at a suitable stage during the producing step of the first catalyst with consideration of the reactivity of the molding auxiliary agent.

The shape of the molded first catalyst is not particularly limited, and can be appropriately selected according to a fowl for using the catalyst. For example, the shape of the first catalyst may be a shape such as a pellet shape, a granular shape, a honeycomb shape, or a sponge shape.

The first catalyst to be used may be subjected to a reduction treatment as a pretreatment. The reduction treatment can be performed in a state where the first catalyst is held at 40 to 600° C. under reducing gas atmosphere, for example. A holding time may be 0.05 to 24 hours, for example. The reducing gas may be hydrogen and carbon monoxide or the like, for example.

By using the catalyst subjected to the reduction treatment, the induction period at an initial stage of a dehydrogenation reaction can be shortened. The induction period at the initial stage of the reaction means a state where there are very few active metals that have been reduced and activated, among active metals contained in the catalyst, and the activity of the catalyst is low.

Subsequently, the second catalyst will be described in detail.

The second catalyst is a catalyst containing Sn and Pt, and the content $C_{S2}$ of Sn in the second catalyst is 12% by mass or more based on the total mass of the second catalyst. It is considered that the second catalyst makes the dehydrogenation reaction to the conjugated diene from the olefin efficiently proceed, and the conjugated diene can be efficiently produced from the alkane by using the second catalyst in combination with the above-mentioned first catalyst.

The reason why the above-mentioned effect is exhibited when the content $C_{S2}$ of the second catalyst is 12% by mass or more is not necessarily clear, but this is considered to be because an acid point of the support is covered with an oxide of Sn, which causes reduction in acid property, thereby suppressing side reactions such as the cracking reaction and polymerization reaction of the olefin. It is also considered that Sn and Pt form bimetallic particles to dilute Pt atoms in the particles, so that the cleavage reaction of a C—C bond caused by the Pt atoms acting on one molecule of the olefin at multiple points is suppressed.

The content $C_{S2}$ of Sn in the second catalyst may be 18% by mass or more based on the total mass of the second catalyst. By the second catalyst, catalyst deterioration is remarkably suppressed.

The content $C_{S2}$ of Sn in the second catalyst may be 40% by mass or less, or 25% by mass or less, based on the total mass of the second catalyst. In the second catalyst, the exposure of a Pt active point is relatively increased, so that higher dehydrogenation activity tends to be obtained.

The content $C_{P2}$ of Pt in the second catalyst may be 0.05% by mass or more, or 0.2% by mass or more, based on the total mass of the second catalyst. By the second catalyst, the amount of platinum per catalyst amount is increased, so that the size of a reactor can be reduced.

The content $C_{P2}$ of Pt in the second catalyst may be 3.0% by mass or less, or 2.0% by mass or less, based on the total mass of the second catalyst. In the second catalyst, Pt particles formed on the catalyst have a size suitable for the dehydrogenation reaction, to increase the surface area of platinum per unit platinum weight, so that a more efficient reaction system can be achieved.

In the second catalyst, the ratio ($C_{S2}/C_{P2}$) of the content $C_{S2}$ to the content $C_{P2}$ is preferably 12 or more, and more preferably 18 or more. The ratio ($C_{S2}/C_{P2}$) may be 50 or less, or 30 or less. When the ratio ($C_{S2}/C_{P2}$) is within the range, catalyst deterioration is further suppressed, so that the dehydrogenation reaction tends to more efficiently proceed.

The second catalyst may contain other metal elements in addition to Sn and Pt. Examples of the other metal elements include Zn, Se, Fe, In, and Al. Each of the metal elements in the second catalyst may be present as a single oxide, may be present as a composite oxide with other metal, or may be present as a metal simple substance.

When the second catalyst contains Al, the content $C_{A2}$ of Al in terms of oxide in the second catalyst may be 20% by mass or more, or 50% by mass or more, based on the total mass of the second catalyst.

When the second catalyst contains Mg, the content $C_{M2}$ of Mg in terms of oxide in the second catalyst may be 1.0% by mass or more, or 5.0% by mass or more, based on the total mass of the second catalyst. The content $C_{M2}$ may be 80% by mass or less, or 50% by mass or less.

The content of each of the metal elements in the second catalyst can be confirmed by analyzing the second catalyst by a method described in the following Examples.

The second catalyst may be a catalyst having a second support and a supported metal supported on the support, for example. At this time, the second catalyst has Pt as the supported metal. In the second catalyst, Sn may be contained in the second support, or may be contained as the supported metal.

The second support may be a metal oxide support containing Al, for example. The metal oxide support may contain Li, Na, K, Mg, Ca, Zn, Fe, Pb, In, Se, Sb, Ni, Ga, Ge, Pt, and Sn or the like, for example, in addition to Al.

Examples of the metal oxide support include the same as the metal oxide supports exemplified as the first support.

The acidity of the second support is preferably near neutrality from the viewpoint of suppressing a side reaction. The acidity of the second support may preferably have a pH of 5.5 to 8.5, and more preferably a pH of 6.0 to 8.0.

The specific surface area of the second support is preferably 30 m$^2$/g or more, and more preferably 50 m$^2$/g or more. The second support can advantageously produce the conjugated diene at high efficiency. The specific surface area of the second support may be 1000 m$^2$/g or less, or 500 m$^2$/g or more. The second support having such a specific surface area has sufficient strength which can be suitably used industrially, and the conjugated diene tends to be produced at higher efficiency by using the second support having such a specific surface area. The specific surface area of the second support is measured with the same method as the method for measuring the specific surface area of the first support.

The second catalyst may have one or two or more of supported metals supported on the second support. A supported metal supported on the second support may be supported as an oxide or a metal simple substance.

Examples of the supported metal supported on the second support include Pt, Sn, Zn, Se, Fe, and In. In the present embodiment, when the second support does not contain Sn, Pt and Sn are contained in the supported metal. When the second support contains Sn, the supported metal may contain Pt.

Examples of a method for supporting the metal on the second support include the same method as the method for supporting the metal on the first support.

The amount of Pt supported on the second support (content of Pt in the second catalyst) is preferably 0.01 parts by mass or more, and more preferably 0.1 parts by mass or more with respect to 100 parts by mass of the second support. The amount of Pt supported on the second support may be 5.0 parts by mass or less, or 3.0 parts by mass or less with respect to 100 parts by mass of the second support. In such an amount of Pt, Pt particles formed on the catalyst have a size suitable for the dehydrogenation reaction, to increase the surface area of platinum per unit platinum weight, so that a more efficient reaction system can be achieved. In such an amount of Pt, high activity can be maintained over a longer period of time while catalyst cost is suppressed.

The degree of dispersion of Pt in the second catalyst may be 1.0% or more, and preferably 5.0% or more. By the second catalyst having such a degree of dispersion of Pt, a side reaction is further suppressed, so that high activity tends to be maintained over a longer period of time. The degree of dispersion of Pt in the second catalyst represents a value measured by a measuring method described in the following Examples.

In one suitable aspect, the second catalyst may be a catalyst having Sn and Pt supported on a second support containing Al (preferably, a metal oxide support containing alumina, or a composite oxide of Al and Mg), or a catalyst having Sn and Pt supported in this order.

In this aspect, the amount of Sn supported on the second support is preferably 12 parts by mass or more, and more preferably 18 parts by mass or more with respect to 100 parts by mass of the second support. When the amount of Sn is within the range, the acid point of the support is more effectively covered with the oxide of Sn, which causes reduction in acid property, thereby suppressing side reactions such as the cracking reaction and polymerization reaction of the olefin, as that higher dehydrogenation activity tends to be obtained.

The amount of Sn supported on the second support is preferably 50 parts by mass or less, and more preferably 30 parts by mass or less with respect to 100 parts by mass of the second support. When the amount of Sn is within the range, catalyst deterioration is further suppressed, so that high activity tends to be maintained over a longer period of time.

The second catalyst may be molded by methods such as an extrusion molding method and a tablet compression method.

The second catalyst may contain a molding auxiliary agent in the range not to deteriorate the physical properties and catalytic performance of the catalyst from the viewpoint of improving moldability in a molding step. The molding auxiliary agent may be at least one selected from the group consisting of a thickener, a surfactant, a humectant, a plasticizer, and a binder raw material, for example. The molding step of molding the dehydrogenation catalyst may be performed at a suitable stage during the producing step of the second catalyst with consideration of the reactivity of the molding auxiliary agent.

The shape of the molded second catalyst is not particularly limited, and can be appropriately selected according to a form for using the catalyst. For example, the shape of the second catalyst may be a shape such as a pellet shape, a granular shape, a honeycomb shape, or a sponge shape. The shape of the second catalyst may be the same as, or different from that of the first catalyst.

The second catalyst to be used may be subjected to a reduction treatment as a pretreatment. The reduction treatment can be performed in a state where the second catalyst is held at 40 to 600° C. under reducing gas atmosphere, for example. A holding time may be 0.05 to 24 hours, for example. The reducing gas may be hydrogen, carbon monoxide or the like, for example.

By using the catalyst subjected to the reduction treatment, the induction period at an initial stage of a dehydrogenation reaction can be shortened. The induction period at the initial stage of the reaction means a state where there are very few active metals that have been reduced and activated, among active metals contained in the catalyst, i.e., the activity of the catalyst is low.

The production method according to the present embodiment includes a step of contacting a raw material gas with a first catalyst and a second catalyst in this order. The step can be conducted using a reactor filled with the first catalyst and the second catalyst, for example.

In the reactor, the first catalyst and the second catalyst may be separately present, or may be present in a mixed state. That is, the reactor may include a first catalyst layer containing the first catalyst and a second catalyst layer containing the second catalyst, or a catalyst layer containing the first catalyst and the second catalyst.

It is considered that, in the catalyst layer in which the first catalyst and the second catalyst are mixed, the raw material gas is brought into contact with the first catalyst, which makes the dehydrogenation reaction of the alkane proceed, and the olefin produced by the dehydrogenation reaction is brought into contact with the second catalyst, which makes the further dehydrogenation reaction proceed, so that the conjugated diene can be efficiently obtained.

When the reactor includes the first catalyst layer and the second catalyst layer, the first catalyst layer can be disposed on the upper stream side (raw material gas inlet side) of the second catalyst layer. Thereby, the dehydrogenation reaction of the first stage is produced in the first catalyst layer, and the dehydrogenation reaction of the second stage is then produced in the second catalyst layer, so that the conjugated diene can be efficiently obtained.

The step may be conducted in a reaction device including a first reactor filled with the first catalyst, and a second reactor filled with the second catalyst, for example. At this time, the first reactor is disposed on the upper stream side of the second reactor.

As the reactor, various reactors used for a gas phase reaction using a solid catalyst can be used. Examples of the reactor include a fixed-bed insulation type reactor, a radial flow type reactor, and a tube-type reactor.

The reaction form of the dehydrogenation reaction may be a fixed-bed type, a moving-bed type, or a fluidized-bed type, for example. Among these, a fixed-bed type is preferred from the viewpoint of equipment cost.

From the viewpoint of reaction efficiency, the reaction temperature of the dehydrogenation reaction, i.e., the temperature in the reactor may be 300 to 800° C., or 500 to 700° C. When the reaction temperature is 500° C. or higher, the amount of production of the conjugated diene tends to be increased. When the reaction temperature is 700° C. or lower, high activity tends to be maintained over a longer period of time.

When the first catalyst and the second catalyst are separately filled, the reaction temperatures in the catalysts may be respectively adjusted. For example, the reaction temperature during the reaction with the first catalyst may be 500 to 700° C., and the reaction temperature during the reaction with the second catalyst may be 500 to 700° C.

The reaction pressure, i.e., the atmospheric pressure in the reactor may be 0.01 to 1 MPa, 0.05 to 0.8 MPa, or 0.1 to 0.5 MPa. When the reaction pressure is within the range, the dehydrogenation reaction is likely to proceed, so that more excellent reaction efficiency tends to be obtained.

When the above step is performed in a continuous reaction form for continuously supplying the raw material gas, a weight hourly space velocity (hereinafter, referred to as "WHSV") may be 0.1 $h^{-1}$ or more, 1.0 $h^{-1}$ or more, 100 $h^{-1}$ or less, or 30 $h^4$ or less. Here, the WHSV is the ratio (supply rate/catalyst mass) of the supply rate (amount of supply/time) of the raw material gas to the catalyst mass (the total mass of the first catalyst and second catalyst) in a continuous reaction device.

When the WHSV is 2.0 $h^{-1}$ or less, the contact time of the alkane contained in the raw material gas with the first catalyst and the second catalyst can be sufficiently secured, so that the dehydrogenation reaction is likely to proceed. When the WHSV is 5.0 $h^{-1}$ or more, the decompositions of the alkane and olefin do not proceed excessively, so that the producing efficiency of the conjugated diene is likely to be improved. The amounts of the raw material gas and catalyst to be used may be appropriately selected in a more preferable range according to reaction conditions and the activity of the catalyst, or the like, and the WHSV is not limited to the range.

As described above, the production method according to the present embodiment can efficiently produce the conjugated diene from the alkane while suppressing the catalyst deterioration. Therefore, the production method according to the present embodiment can efficiently produce the conjugated diene while reducing the frequency of catalyst reproduction. Because of this, the production method according to the present embodiment is very useful when the conjugated diene is industrially produced.

While the suitable embodiment of the present invention has been described above, the present invention is not limited to the embodiment. For example, one aspect of the present invention may be a reaction device for obtaining a product gas containing a conjugated diene from a raw material gas containing an alkane. The reaction device may include a first catalyst layer containing a first catalyst and a second catalyst layer containing a second catalyst in one aspect. The reaction device may include a catalyst layer containing a first catalyst and a second catalyst in the other aspect.

EXAMPLES

Hereinafter, the present invention will be more specifically described with reference to Examples, but the present invention is not limited to Examples.

Catalyst Synthesis Example 1

<Preparation of Catalyst Precursor A-1>

A solution in which 0.24 g $SnCl_2.2H_2O$ was dissolved in 50 mL of EtOH was added into 2.0 g of an alumina support classified to 20 to 60 meshes (NEOBEADS GB-13, manufactured by Mizusawa Industrial Chemicals, Ltd., pH of a suspension having a concentration of 1% by mass in water: 7.9). The obtained mixed solution was stirred at room temperature for 30 minutes using a rotary evaporator, and EtOH was then removed under reduced pressure. The obtained solid was dried at 130° C. in an oven overnight. Next, the dried solid was fired at three stages (at 130° C. for 30 minutes, at 550° C. for 3 hours, and at 800° C. for 3 hours) under an air flow to obtain a catalyst precursor A-1 in which Sn was supported on an alumina support.

<Preparation of Catalyst A-1>

2.0 g of a catalyst precursor A-1, and an aqueous solution in which 53.6 mg of $H_2PtCl_6.2H_2O$ was dissolved in 11 mL of water were mixed. The obtained mixed solution was stirred at 40° C. for 30 minutes using a rotary evaporator, and water was then removed under reduced pressure while the mixed solution was stirred. The obtained solid was dried at 130° C. in an oven overnight. Next, the dried solid was fired at two stages (at 130° C. for 30 minutes, and at 550° C. for 3 hours) under an air flow, and then subjected to hydrogen reduction at 550° C. for 3 hours, to obtain a catalyst A-1.

In the obtained catalyst A-1, the content of Sn was 5.8% by mass based on the total mass of the catalyst; and the content of Pt was 1.0% by mass based on the total mass of the catalyst. In the catalyst A-1, the degree of dispersion of Pt was 32.9%.

[Analysis Method of Catalyst]

In the present Examples, the content of the metal element in the catalyst was measured with an X-ray fluorescence analysis method (XRF). The X-ray fluorescence analysis was performed using a measuring device PW2400 (manufactured by PANalytical), and the content was quantified using standardless quantitative calculation program UniQuant4. A measurement sample for XRF was prepared as follows. 125 mg of a sample (for example, catalyst A-1), and 125 mg of cellulose (binder) were measured in an agate mortar, and mixed for 15 minutes to obtain a mixture, and the mixture was then put into a tablet molding machine having a diameter of 20 mm, to subject the mixture to pressure molding on conditions of 300 kgf·cm$^{-2}$ for 10 minutes.

The degree of dispersion of Pt was measured by a method for measuring the degree of dispersion of metal using CO as adsorption species. A device and measurement conditions or the like will be shown below.

Device: device for measuring degree of dispersion of metal R-6011 manufactured by Ohkura Riken Co., LTD.

Gas flow rate: 30 mL/min (helium, hydrogen)

Amount of sample: about 0.1 g (precisely measured to four decimal places)

Pretreatment: A temperature was risen to 400° C. over 1 hour under a hydrogen stream, to perform a reduction treatment at 400° C. for 60 minutes. The gas was then changed from hydrogen to helium, to purge the hydrogen at 400° C. for 30 minutes, and the temperature was then decreased to room temperature under a helium stream. After a detector was stabilized at room temperature, CO pulsing was performed.

Measurement conditions: Carbon monoxide was pulse-injected by 0.0929 cm$^3$ at room temperature (27° C.) under a stream of normal pressure helium gas to measure the amount of adsorption thereof. The adsorption was performed a number of times until the adsorption was saturated (at least 3 times, at most 15 times).

Catalyst Synthesis Example 2

In preparing a catalyst precursor, a catalyst was prepared in the same manner as in Catalyst Synthesis Example 1 except that the blending amount of $SnCl_2.2H_2O$ was set to 0.45 g to afford a catalyst A-2.

In the obtained catalyst A-2, the content of Sn was 10.2% by mass based on the total mass of the catalyst, and the content of Pt was 1.0% by mass based on the total mass of the catalyst. In the catalyst A-2, the degree of dispersion of Pt was 26.2%.

Catalyst Synthesis Example 3

In preparing a catalyst precursor, a catalyst was prepared in the same manner as in Catalyst Synthesis Example 1 except that the blending amount of $SnCl_2.2H_2O$ was set to 0.62 g to afford a catalyst A-3.

In the obtained catalyst A-3, the content of Sn was 13.4% by mass based on the total mass of the catalyst, and the content of Pt was 1.0% by mass based on the total mass of the catalyst. In the catalyst A-3, the degree of dispersion of Pt was 15.3%.

Catalyst Synthesis Example 4

In preparing a catalyst precursor, a catalyst was prepared in the same manner as in Catalyst Synthesis Example 1 except that the blending amount of $SnCl_2.2H_2O$ was set to 0.90 g to afford a catalyst A-4.

In the obtained catalyst A-4, the content of Sn was 18.1% by mass based on the total mass of the catalyst, and the content of Pt was 1.0% by mass based on the total mass of the catalyst. In the catalyst A-4, the degree of dispersion of Pt was 9.1%.

(Reference Test 1-1: Dehydrogenation Reaction of Alkane)

A tube-type reactor was filled with 0.5 g of a catalyst A-1, and the reaction tube was connected to a fixed-bed circulation type reaction device. Next, while a mixed gas of hydrogen and He (hydrogen : He=4:6 (mole ratio)) was circulated at a rate of 50 mL/min, the temperature of the reactor was raised to 550° C., and the reactor was held at the temperature for 1 hour. Then, a mixed gas (raw material gas) of n-butane, He, and water was supplied to the reactor, to subject n-butane in the raw material gas to a dehydrogenation reaction. Herein, the male ratio of n-butane, He, and water in the raw material gas was adjusted to 1:4:3. The supply rate of the raw material gas to the reactor was adjusted to 99 mL/min. The WHSV with respect to the total amount of the catalyst was adjusted to $3.913.^{-1}$. The pressure of the raw material gas of the tube-type reactor was adjusted to atmospheric pressure.

At a point of time when 20 minutes elapsed from the start of the reaction, a product material (product gas) of the dehydrogenation reaction was extracted from the tube-type reactor. At a point of time when 360 minutes elapsed from the start of the reaction, a product material (product gas) of the dehydrogenation reaction was extracted from the tube-type reactor. At the start of the reaction, the supply of the raw material gas was started. The product gas extracted at each time was analyzed using a gas chromatograph (TCD-GC) provided with a thermal conductivity detector. As a result of analysis, the product gas was confirmed to contain 1,3-butadiene. The concentration (unit: % by mass) of butene and the concentration (unit: % by mass) of 1,3-butadiene in the product gas extracted at each time were quantified based on the gas chromatograph.

From the concentrations of butene and 1,3-butadiene in the product gas, the yield of butene (butene yield) and the yield of 1,3-butadiene (butadiene yield) at each time were calculated. The butadiene yield is defined by the following formula (4); and the butene yield is defined by the following formula (5).

$$R_{Y1}=M_b/M_0\times 100 \quad (4)$$

$$R_{Y2}=M_P/M_0\times 100 \quad (5)$$

$R_{Y1}$ in the formula (4) is the butadiene yield; $M_0$ is the number of moles of n-butane in the raw material gas; and $M_b$ is the number of moles of 1,3-butadiene in the product gas.

$R_{Y2}$ in the formula (5) is the butene yield; $M_0$ is the number of moles of n-butane in the raw material gas; and $M_P$ is the number of moles of 1-butene, t-2-butene, and c-2 butene in the product gas.

As a result of calculation, at a point of time when 20 minutes elapsed, the total (hereinafter, referred to as total yield) of the butene yield and butadiene yield was 47.6%, and at a point of time when 360 minutes elapsed, the total yield was 26.0%. The butene yield and the butadiene yield at a point of time when 20 minutes elapsed were respectively 40.9% and 6.7%, and the butene yield and the butadiene yield at a point of time when 360 minutes elapsed were respectively 20.4% and 5.6%.

(Reference Test 1-2)

The dehydrogenation reaction of n-butane and the analysis of a product gas were performed by the same operation as that of Example 1 except that a catalyst A-2 was used in place of the catalyst A-1. The total yield of butene and butadiene at a point of time when 20 minutes elapsed from the start of the reaction was 52.4%, and the total yield at a point of time when 360 minutes elapsed was 40.9%. A butene yield and a butadiene yield at a point of time when 20 minutes elapsed were respectively 45.5% and 6.9%, and a butene yield and a butadiene yield at a point of time when 360 minutes elapsed were respectively 34.3% and 6.6%.

(Reference Test 1-3)

The dehydrogenation reaction of n-butane and the analysis of a product gas were performed by the same operation as that of Example 1 except that a catalyst A-3 was used in place of the catalyst A-1. The total yield of butene and butadiene at a point of time when 20 minutes elapsed from the start of the reaction was 14.6%, and the total yield at a point of time when 360 minutes elapsed was 13.3%. A butene yield and a butadiene yield at a point of time when 20 minutes elapsed were respectively 10.3% and 4.3%, and a butene yield and a butadiene yield at a point of time when 360 minutes elapsed were respectively 9.1% and 4.2%.

(Reference Test 1-4)

The dehydrogenation reaction of n-butane and the analysis of a product gas were performed by the same operation as that of Example 1 except that a catalyst A-3 was used in place of the catalyst A-1. The total yield of butene and butadiene at a point of time when 20 minutes elapsed from the start of the reaction was 1.9%, and butene and butadiene were hardly measured from the product gas at a point of time when 360 minutes elapsed. A butene yield and a butadiene yield at a point of time when 20 minutes elapsed were respectively 1.4% and 0.5%.

The results of Reference Tests 1-1 to 1-4 are shown in Table 1.

TABLE 1

| | | Reference Test 1-1 | Reference Test 1-2 | Reference Test 1-3 | Reference Test 1-4 |
|---|---|---|---|---|---|
| Catalyst composition | Catalyst | Catalyst A-1 | Catalyst A-2 | Catalyst A-3 | Catalyst A-4 |
| | Amount of Pt (% by mass) | 1.0 | 1.0 | 1.0 | 1.0 |
| | Amount of Sn (% by mass) | 5.8 | 10.2 | 13.4 | 18.1 |
| | Degree of dispersion of Pt (%) | 32.9 | 26.2 | 15.3 | 9.1 |
| Reaction conditions | Temperature (° C.) | 550 | 550 | 550 | 550 |
| | Pressure (MPaG) | 0 | 0 | 0 | 0 |
| | WHSV ($h^{-1}$) | 3.9 | 3.9 | 3.9 | 3.9 |
| | Raw material mixing ratio (mole ratio), n-butane/He/$H_2O$ | 1:4:3 | 1:4:3 | 1:4:3 | 1:4:3 |
| Reaction results | Total yield After 20 minutes | 47.6 | 52.4 | 14.6 | 1.9 |
| | ($R_{Y1} + R_{Y2}$) After 360 minutes | 26.0 | 40.9 | 13.3 | — |

(Reference Test 2-1)

The dehydrogenation reaction of 1-butene and the analysis of a product gas were performed by the same operation as that of Reference Test 1-1 except that a mixed gas of 1-butene, He, and water (the mole ratio of 1-butene, He, and water was 1:4:3) was used as a raw material gas, to obtain the yield of 1,3-butadiene (butadiene yield) at a point of time when 20 minutes elapsed from the start of the reaction and at a point of time when 360 minutes elapsed. The butadiene yield is defined by the following formula (6).

$$R_{Y3} = Mb/M'_0 \times 100 \quad (6)$$

$R_{Y3}$ in the formula (6) is the butadiene yield. $M'_0$ is the number of moles of 1-butene in the raw material gas.

As a result of analysis, a butadiene yield at a point of time when 20 minutes elapsed from the start of the reaction was 20.5%, and a butadiene yield at a point of time when 360 minutes elapsed was 7.9%.

(Reference Test 2-2)

The dehydrogenation reaction of 1-butene and the analysis of a product gas were' performed by the same operation as that of Reference Test 2-1 except that a catalyst A-2 was used in place of the catalyst A-1. A butadiene yield at a point of time when 20 minutes elapsed from the start of the reaction was 21.4%, and a butadiene yield at a point of time when 360 minutes elapsed was 17.9%.

(Reference Test 2-3)

The dehydrogenation reaction of 1-butene and the analysis of a product gas were performed by the same operation as that of Reference Test 2-1 except that a catalyst A-3 was used in place of the catalyst A-1. A butadiene yield at a point of time when 20 minutes elapsed from the start of the reaction was 21.5%, and a butadiene yield at a point of time when 360 minutes elapsed was 23.9%.

(Reference Test 2-4)

The dehydrogenation reaction of 1-butene and the analysis of a product gas were performed by the same operation as that of Reference Test 2-1 except that a catalyst A-4 was used in place of the catalyst A-1. A butadiene yield at a point of time when 20 minutes elapsed from the start of the reaction was 18.4%, and a butadiene yield at a point of time when 360 minutes elapsed was 18.2%.

The results of Reference Tests 2-1 to 2-4 are shown in Table 2.

(product gas outlet side) of the tube-type reactor was filled with 1.0 g of a catalyst A-4 (second catalyst) for use in a second catalyst layer. Subsequently, the reaction tube was connected to a fixed-bed circulation type reaction device. Next, while a mixed gas of hydrogen and $N_2$ (hydrogen : $N_2$=5:5 (mole ratio)) was circulated at a rate of 50 mL/min, the temperature of the upper layer of the reactor was raised to 550° C., and the reactor was held at the temperature for 1 hour. Simultaneously, the temperature of the lower layer of the reactor was raised to 600° C., and the reactor was held at the temperature for 1 hour. Then, a mixed gas (raw material gas) of n-butane, $N_2$, and water was supplied to the reactor, to subject n-butane in the raw material gas to a dehydrogenation reaction. Herein, the mole ratio of n-butane, $N_2$, and water in the raw material gas was adjusted to 1:5:3. The supply rate of the raw material gas to the tube-type reactor was adjusted to 62 mL/min. A WHSV with respect to the total amount of the catalyst was adjusted to 0.5 $h^{-1}$. The pressure of the raw material gas of the tube-type reactor was adjusted to atmospheric pressure.

At a point of time when 60 minutes elapsed from the start of the reaction, a product material (product gas) of the dehydrogenation reaction was extracted from the tube-type reactor. At a point of time when 300 minutes elapsed from the start of the reaction, a product material (product gas) of the dehydrogenation reaction was extracted from the tube-type reactor. At the start of the reaction, the supply of the raw material gas was started. The product gas extracted at each time was analyzed using a gas chromatograph (TCD-GC) provided with a thermal conductivity detector. As a result of analysis, the product gas was confirmed to contain 1,3-butadiene. The concentration (unit: % by mass) of 1,3-butadiene in the product gas extracted at each time was quantified based on the gas chromatograph.

From the concentration of 1,3-butadiene in the product gas, the yield of 1,3-butadiene (butadiene yield) at each time was calculated. The results are shown in the following Table 1. The butadiene yield is defined by the following formula (4).

$$R_{Y1} = M_b/M_0 \times 100 \quad (4)$$

$R_{Y1}$ in the formula (4) is the butadiene yield. $M_0$ is the number of moles of n-butane in the raw material gas, and $M_b$ is the number of moles of 1,3-butadiene in the product gas.

TABLE 2

|  |  | Reference Test 2-1 | Reference Test 2-2 | Reference Test 2-3 | Reference Test 2-4 |
|---|---|---|---|---|---|
| Catalyst composition | Catalyst | Catalyst A-1 | Catalyst A-2 | Catalyst A-3 | Catalyst A-4 |
|  | Amount of Pt (% by mass) | 1.0 | 1.0 | 1.0 | 1.0 |
|  | Amount of Sn (% by mass) | 5.8 | 10.2 | 13.4 | 18.1 |
|  | Degree of dispersion of Pt (%) | 32.9 | 26.2 | 15.3 | 9.1 |
| Reaction conditions | Temperature (° C.) | 550 | 550 | 550 | 550 |
|  | Pressure (MPaG) | 0 | 0 | 0 | 0 |
|  | WHSV ($h^{-1}$) | 3.9 | 3.9 | 3.9 | 3.9 |
|  | Raw material mixing ratio (mole ratio), 1-butene/He/$H_2O$ | 1:4:3 | 1:4:3 | 1:4:3 | 1:4:3 |
| Reaction results | Yield $R_{Y3}$ After 20 minutes | 20.5 | 21.4 | 21.5 | 18.4 |
|  | After 360 minutes | 7.9 | 17.9 | 23.9 | 18.2 |
|  | (Yield after 360 minutes)/(Yield after 20 minutes) | 0.38 | 0.84 | 1.12 | 0.99 |

Example 1

The upper layer (raw material gas inlet side) of a tube-type reactor was filled with 1.0 g of a catalyst A-2 (first catalyst) for use in a first catalyst layer. Next, the lower layer As a result of calculation, the butadiene yield at a point of time when 60 minutes elapsed was 16.5%; and the butadiene yield at a point of time when 300 minutes elapsed was 15.3%.

Catalyst Synthesis Example 5

<Preparation of Catalyst Precursor B-1>

105.5 g of Al(NO$_3$)$_3$·9H$_2$O and 36.1 g of Mg(NO$_3$)$_2$·6H$_2$O were added into 1 L of ion exchange water, followed by vigorous stirring. While the aqueous solution was stirred, a solution obtained by diluting concentrated ammonia water two-fold was dropped at a rate of 0.1 mL/s until the pH of the solution was set to 10, and the solution was left for 30 minutes after being stirred for 30 minutes. The precipitate was filtered, and washed with 1.3 L of ion exchange water twice. Then, the obtained precipitate was dried at 130° C. in an oven overnight. Finally, the dried solid was fired at three stages (at 300° C. for 1 hour, at 500° C. for 2 hours, and at 800° C. for 4 hours) under an air flow to obtain a catalyst precursor B-1.

<Preparation of Catalyst B-1>

159.3 mg of H$_2$PtCl$_6$·2H$_2$O and 624.7 mg of SnCl$_2$·H$_2$O were dissolved in a 1 mol/L HCl aqueous solution, and 6.0 g of the catalyst precursor B-1 was added thereto. The obtained mixed solution was stirred at 40° C. for 1 hour using a rotary evaporator, and water was then removed under reduced pressure while the mixed solution was stirred. The obtained solid was dried at 130° C. in an oven overnight. Next, the dried solid was fired at two stages (at 130° C. for 1 hour, and at 550° C. for 3 hours) under an air flow. Then, the fired product was tablet-compressed to 0.5 mm to 1.0 mm, and then subjected to hydrogen reduction at 550° C. for 3 hours, to obtain a catalyst B-1.

In the obtained catalyst B-1, the content of Sn was 5.5% by mass based on the total mass of the catalyst, and the content of Pt was 1.0% by mass based on the total mass of the catalyst.

Example 2

The dehydrogenation reaction of n-butane and the analysis of a product gas were performed by the same operation as that of Example 1 except that a catalyst B-1 was used as a first catalyst in place of the catalyst A-2. A butadiene yield at a point of time when 60 minutes elapsed from the start of the reaction was 16.4%, and a butadiene yield at a point of time when 300 minutes elapsed was 15.2%.

Comparative Example 1

The dehydrogenation reaction of n-butane and the analysis of a product gas were performed by the same operation as that of Example 1 except that both the upper and lower layers of a tube-type reactor were filled with a catalyst B-1. A butadiene yield at a point of time when 60 minutes elapsed from the start of the reaction was 13.3%, and a butadiene yield at a point of time when 300 minutes elapsed was 11.3%.

Comparative Example 2

The dehydrogenation reaction of n-butane and the analysis of a product gas were performed by the same operation as that of Example 1 except that both the upper and lower layers of a tube-type reactor were filled with a catalyst A-4. A butadiene yield at a point of time when 60 minutes elapsed from the start of the reaction was 4.3%, and at a point of time when 300 minutes elapsed, 1,3-butadiene was hardly measured from the product gas.

The results of Examples 1 and 2 and Comparative Examples 1 and 2 are shown in Table 3.

TABLE 3

| | | | | Example 1 | Example 2 | Comparative Example 1 | Comparative Example 2 |
|---|---|---|---|---|---|---|---|
| Upper layer | | Catalyst | | Catalyst A-2 | Catalyst B-1 | Catalyst B-1 | Catalyst A-4 |
| | | Amount of Pt | % by mass | 1.0 | 1.0 | 1.0 | 1.0 |
| | | Amount of Sn | % by mass | 10.2 | 5.5 | 5.5 | 18.1 |
| Lower layer | | Catalyst | | Catalyst A-4 | Catalyst A-4 | Catalyst B-1 | Catalyst A-4 |
| | | Amount of Pt | % by mass | 1.0 | 1.0 | 1.0 | 1.0 |
| | | Amount of Sn | % by mass | 18.1 | 18.1 | 5.5 | 18.1 |
| Reaction conditions | Temperature | Upper layer | ° C. | 550 | 550 | 550 | 600 |
| | | Lower layer | ° C. | 600 | 600 | 600 | 600 |
| | | Pressure | MPaG | 0 | 0 | 0 | 0 |
| | | WHSV | h$^{-1}$ | 0.5 | 0.5 | 0.5 | 0.5 |
| | | Raw material mixing ratio (C$_4$/N$_2$/H$_2$O) | mole ratio | 1:5:3 | 1:5:3 | 1:5:3 | 1:5:3 |
| Evaluation results | R$_Y$ | After 60 minutes | % | 16.5 | 16.4 | 13.3 | 4.3 |
| | | After 300 minutes | % | 15.3 | 15.2 | 11.3 | — |
| | | (Yield after 300 minutes)/(Yield after 60 minutes) | — | 0.93 | 0.93 | 0.85 | — |

The invention claimed is:

1. A method for producing a conjugated diene, comprising a step of contacting a raw material gas containing an alkane with a first catalyst and a second catalyst in this order to obtain a product gas containing a conjugated diene, wherein
the first catalyst contains Sn and Pt, and a content of Sn in the first catalyst is less than 12% by mass based on a total mass of the first catalyst, and
the second catalyst contains Sn and Pt, and a content of Sn in the second catalyst is 12% by mass or more based on a total mass of the second catalyst.

2. The method according to claim 1, wherein
the first catalyst has a first support containing Al, and
the second catalyst has a second support containing Al.

3. The method according to claim 1, wherein
a content of Pt in the first catalyst is 0.05% by mass or more and 3% by mass or less based on the total mass of the first catalyst, and a content of Pt in the second catalyst is 0.05% by mass or more and 3% by mass or less based on the total mass of the second catalyst.

4. The method according to claim 1, wherein the alkane is an alkane having 4 to 10 carbon atoms.

5. The method according to claim 1, wherein the alkane is butane, and the conjugated diene is butadiene.

* * * * *